United States Patent
Wong (10) Patent No.: US 9,580,484 B2
(45) Date of Patent: Feb. 28, 2017

(54) **MEANS AND METHOD FOR EXPRESSION OF AUTHENTIC HUMAN EPIDERMAL GROWTH FACTOR AND/OR BASIC FIBROLAST GROWTH FACTOR IN CYTOPLASM AND/OR CULTURE MEDIUM OF *ESCHERICHIA COLI***

(71) Applicant: Wan Keung Raymond Wong, Clear Water Bay (HK)

(72) Inventor: Wan Keung Raymond Wong, Clear Water Bay (HK)

( * ) Notice: Subject to any disclaimer, the term of this patent is extended or adjusted under 35 U.S.C. 154(b) by 0 days.

(21) Appl. No.: 14/781,614

(22) PCT Filed: Feb. 25, 2014

(86) PCT No.: PCT/CN2014/072531
§ 371 (c)(1),
(2) Date: Oct. 1, 2015

(87) PCT Pub. No.: WO2014/161405
PCT Pub. Date: Oct. 9, 2014

(65) Prior Publication Data
US 2016/0060318 A1 Mar. 3, 2016

Related U.S. Application Data
(60) Provisional application No. 61/808,062, filed on Apr. 3, 2013.

(51) Int. Cl.
*C12N 15/70* (2006.01)
*C07K 14/50* (2006.01)
*C07K 14/485* (2006.01)

(52) U.S. Cl.
CPC .......... *C07K 14/503* (2013.01); *C07K 14/485* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 5,646,015 A | 7/1997 | Wong et al. | |
| 7,517,528 B2 | 4/2009 | Wong et al. | |
| 2001/0051148 A1* | 12/2001 | Tremblay | A61K 35/34 424/93.1 |
| 2007/0092489 A1* | 4/2007 | Fishbein | A61K 47/48107 424/93.2 |
| 2008/0254512 A1* | 10/2008 | Capon | A61K 47/48507 435/69.6 |

OTHER PUBLICATIONS

Alibolandi, et al., Purification and Refolding of Overexpressed Human Basic Fibroblast Growth Factor in *Escherichia coli* SAGE-Hindawi Access to Research, Biotechnology Research International, vol. 2011, Article ID 973741, Jun. 8, 2011.
Andrades, et al., Production of a Recombinant Human Basic Fibroblast Growth Factor with a Collagen Binding Domain, Protoplasma, 218: 95-103, Springer-Verlag, Austria, 2001.
Barr, et al., Expression and Processing of Biologically Active Fibroblast Growth Factors in the Yeast *Saccharomyces cerevzslae*, The Journal of Biological Chemistry, vol. 263, No. 31, Issue of Nov. 5, pp. 16471-16478, 1988, U.S.A.
Bikfalvi, et al., Biological Roles of Fibroblast Growth Factor-2, Endocrine Reviews, vol. 18, No. 1, 1997, U.S.A.
Chan, et al., Cloning and Characterization of a Novel Cellobiase Gene, cba3, Encoding the First Known β-Glucosidase of Glycoside Hydrolase Family 1 of *Cellulomonas biazotea*, Gene, vol. 493 (2012), pp. 52-61, Elsevier (2012).
Cottingham, et al., A Method for the Amidation of Recombinant Peptides Expressed as Intein Fusion Proteins in *Escherichia coli*, Nature Biotechnology, vol. 19, pp. 974-977, Oct. 2001, Nature Publishing Group.
Elleuche, et al., Inteins, Valuable Genetic Elements in Molecular Biology and Biotechnology, Appl Microbiol Biotechnical, 87, pp. 479-489, 2010, Springer.
Esipov, et al., Production of Recombinant Human Epidermal Growth Factor using Ssp dnaB Mini-Intein System, Protein Expression and Purification, vol. 61, pp. 1-6, 2008, Elsevier.
Ferrer-Miralles, et al., Microbial Factories for Recombinant Pharmaceuticals, Microbial Cell Factories, vol. 8, pp. 17-25, 2009.
Fu, et al., Cell Death Caused by Hyper-Expression of a Secretory Exoglucanase in *Escherichia coli*, Protein Expression & Purification, vol. 42, pp. 67-77, 2005, Elsevier.
Fu, et al., A Two-Stage Refinement Approach for the Enhancement of Excretory Production of an Exoglucanase from *Escherichia coli*, Protein Expression & Purification, vol. 48, pp. 205-214, 2006, Elsevier.
Garke, et al., Preparative Two-Step Purification of Recombinant Human Basic Fibroblast Growth Factor from High-Cell-Density Cultivation of *Eshericia coli*, Journal of Chromatography B, vol. 737, pp. 25-38, 2000, Elsevier.
Huang, et al., Human Epidermal Growth Factor Excreted by Recombinant *Escherichia coli* K-12 has the Correct N-terminus and is Fully Bioactive, Process Biochemistry, vol. 35, pp. 1-5, 1999, Elsevier.
Ingham, et al., A Versatile System for the Expression of Nomuodified Bacteriocins in *Escherichia coli*, Journal of Applied Microbiology, vol. 98, pp. 676-686, 2005.

(Continued)

*Primary Examiner* — Jim Ketter
(74) *Attorney, Agent, or Firm* — Heslin, Rothenberg, Farley & Mesiti, P.C.; Kellie S. Fredericks; Melvin Li (57) ABSTRACT

The present invention relates to an engineered biological system, and in particular an *Escherichia coli* host. The host is incorporated with a DNA construct for production of at least a first polypeptide. The first polypeptide may be an authentic basic fibroblast growth factor (bFGF). The DNA construct has an insert including, for example, in the sequence of, an expression cassette, an intein sequence and DNA coding for the first polypeptide. The DNA construct is configured to effect the host to secrete the basic fibroblast growth factor (bFGF) in the cytoplasm of the host and/or to excrete to cell medium in which the host is cultured.

15 Claims, 4 Drawing Sheets

(56) References Cited

OTHER PUBLICATIONS

Kwong, et al., Authentic Human Basic Fibroblast Growth Factor Produced by Secretion in *Bacillus subtilis*, Appl Microbiol Biotechnical, vol. 97, pp. 6803-6811, 2013, Springer.
Lam, et al., Enhancement of Extracellular Production of a *Cellulomonas fimi* Exoglucanase in *Escherichia coli* by the Reduction of Promoter Strength, Enzyme and Microbial Technology, vol. 20, pp. 482-488, 1997, Elsevier.
Lee, et al., Genetic Studies on the Inability of β-Galactosidase to Be Translocated Across the *Escherichia coli* Cytoplasmic Membrane, Journal of Bacteriology, vol. 171, No. 9, pp. 4609-4616, Sep. 1989.
Li, Yifeng, Self-Cleaving Fusion Tags for Recombinant Protein Production, Biotechnology Letters, vol. 33, pp. 869-881, 2011, Springer.
Mirzahoseini, et al., Differential Expression of Human Basic Fibroblast Growth Factor in *Escherichia coli*: Potential Role of Promoter, World Journal of Microbiology & Biotechnology, vol. 20, pp. 161-165, 2004, Khwer Academic Publishers, Netherlands.
Mu, et al., High-Level Expression, Purification, and Characterization of Recombinant Humas Basic Fibroblast Growth Factor in *Pichia pastoris*, Protein Expression & Purification, vol. 59, pp. 282-288, 2008, Elsevier.
Nakayama, et al., Efficient Secretion of the Authentic Mature Elliman Growth Hormone by *Bacillus subtilis*, pp. 123-134, 1988, Elsevier.
Sellke, et al., Therapeutic Angiogenesis with Basic Fibroblast Growth Factor: Technique and Early Results, The Annals of Thoracic Surgery, vol. 65, pp. 1540-1544, 1998.
Sheng, et al., Expression and Purification of a Biologically Active Basic Fibroblast Growth Factor Fusion Protein, Protein Expression and Purification, vol. 27, pp. 267-271, 2003, Elsevier Science (USA).
Sivakesava, et al., Production of Excreted Human Epidermal Growth Factor (hEGF) by an Efficient Recombinant *Escherichia coli* System, Process Biochemistry, vol. 34, pp. 893-900, 1999, Elsevier.
Wang, et al., Expression of Intein-Tagged Fusion Protein and Its Applications in Downstream Processing, Journal of Chemical Technology and Biotechnology, vol. 85, pp. 11-18, 2010.
Wang, et al., Enhancement of Excretory Production of an Exoglucanase from *Escherichia coli* with Phage Shock Protein a (PspA) Overexpression, Journal of Microbiology and Biotechnology, 21(6), pp. 637-645, 2011.
Wong, et al., Application of Recombinant Microbial Systems to the Production of Commercially Valuable Proteins, Research Journal of Biotechnology, vol. 3(3), Aug. 2008.
Wong, et al., Applications, and Efficient Large-Scale Production, of Recombinant Human Epidermal Growth Factor, Biotechnology & Genetic Engineering Reviews, vol. 18, Jul. 2001.
Wong, et al., Cloning, Expression, and Characterization of Diuretic Hormone *Manduca* diuresin from *Manduca sexta* in *Escherichia coli*, Protein Expression and Purification, vol. 29, pp. 51-57, 2003, Elsevier.
Wong, et al., Engineering of Efficient *Escherichia coli* Excretion Systems for the Production of Heterologous Proteins for Commercial Applications, Recent Patents on Chemical Engineering, vol. 5, pp. 45-55, 2012, Bentham Science Publishers.
Goeddel, et al., Expression in *Escherichia coli* of Chemically Synthesized Genes for Human Insulin, Proceedings of the National Academy of Sciences, USA, vol. 76, No. 1, pp. 106-110, Jan. 1979.
Wong, et al., Extracellular Expression of Human Epidermal Growth Factor Encoded by an *Escherichia coli* K-12 Plasmid Stabilized by the ytl2-mcR System of *Salmonella typhimurium*, Journal of Industrial Microbiology & Biotechnology, vol. 21, pp. 31-36, 1998.

\* cited by examiner

FIG. 1

Table 1. Oligonucleotides employed in experiments

| SEQ ID NO. | Primer | Sequence |
|---|---|---|
| 1 | P1 | 5'- CAAGAATTCGCATACTTACTCCCCATCCCCCTGTTTACAC -3' |
| 2 | P2 | 5'- GCCGCCATCCTCTGGCAAGGCTGGGGCCTGCGCTACCGTAGCGAAACC -3' |
| 3 | P3 | 5'- GGTTTCGCTACCGTAGCGCAGGCCCCAGCCTTGCCAGAGGATGGCGGCAGCGGC -3' |
| 4 | P4 | 5'- CCCAATTCTTAAAAAAAAGCCCGCTCATTAGGCGGGCTGCTTAATTAATTA -3' |
| 5 | P5 | 5'-CTTTTTCTTCCAATGTCTGCTAAGAGCTAATGAAATTAATTCCTGCAGGCTTAATTAATTAAGCAGCCCGCC -3' |
| 6 | P6 | 5'-CTATCGCGATTGCAGTGGCACTGGCTGGTTTCGCTACCGTAGCGCAGGCCTGCTTTGCCAAGGGTACCAATGTTTTAATG -3' |
| 7 | P7 | 5'- GCCGCTGCCGCCATCCTCTGGCAAGGCTGGGTTCTGTACAACAACCTGAGATCCAAGCAAAAAC -3' |
| 8 | P8 | 5'- GTTTTTGCTTGGATCTCAGGTTGTTGTACAGAACCCAGCCTTGCCAGAGGATGGCGGCAGCGGC -3' |
| 9 | P9 | 5'- CCTGTTTTGGATCCAAGTTTATACTGCCCAGTGCGTTTC -3' |
| 10 | P10 | 5'- CAGCTATCGCGATTGCAGTGGCACTGGCTGGTTTCG -3' |
| 11 | P11 | 5'- CATTGGTACCCTTGGCAAAGCAGCGCAGTTCCCACCACTTCAGGTCTCGGTAC -3' |

FIG. 2

Table 2. Analysis of purified bFGF by liquid chromatography-tandem mass spectrometry bFGF purified from culture medium of JM101 [pWK3R] transformant[a]

| Peptide[b] | Mr(Calc)[c] | Mr(Expt)[d] | Ion Score | SEQ ID NO. |
|---|---|---|---|---|
| NH2-PALPEDGGSGAFPPGHFK | 1779 | 1780 | 55 | 12 |
| AILFLPMSAK.S | 1090 | 1089 | 46 | 13 |
| TGPGQKAILFLPMSAKS-COOH | `1744 | 1744 | 15 | 14 | bFGF purified from cell lysate of JM101 [pWK3R] transformant[a]

| Peptide[b] | Mr(Calc)[c] | Mr(Expt)[d] | Ion Score | SEQ ID NO. |
|---|---|---|---|---|
| NH2-PALPEDGGSGAFPPGHFK | 1779 | 1780 | 76 | 12 |
| AILFLPMSAK.S | 1090 | 1089 | 57 | 13 |
| TGPGQKAILFLPMSAKS-COOH | `1744 | 1744 | 12 | 14 |

[a]Conditions for growth and induction of JM101 [pWK3R] culture were described in Methods.
[b]Subsequent to partial trypsin digestion of the purified bFGF, the N-terminal and C-terminal sequences were identified by the Mascot search engine.
[c]Theoretical mass-to-charge ratio of the peptide
[d]Experimental mass-to-charge ratio of the peptide

MEANS AND METHOD FOR EXPRESSION OF AUTHENTIC HUMAN EPIDERMAL GROWTH FACTOR AND/OR BASIC FIBROLAST GROWTH FACTOR IN CYTOPLASM AND/OR CULTURE MEDIUM OF *ESCHERICHIA COLI*

CROSS REFERENCE TO RELATED APPLICATIONS

This application is a national stage filing under 35 U.S.C. §371 of International Application No. PCT/CN2014/072531 filed on Feb. 25, 2014, and published in English on Oct. 9, 2014 as WO 2014/161405 A1 and claims priority from U.S. Patent Application No. 61/808,062 filed on Apr. 3, 2013, the entire disclosure of these applications being hereby incorporated herein by reference.

SEQUENCE LISTING

The instant application contains a Sequence Listing and is hereby incorporated by reference in its entirety.

FIELD OF THE INVENTION

The present invention is concerned with means and method for expression of authentic polypeptides of human epidermal growth factor and/or basic fibroblast growth factor in cytoplasm and/or culture medium of *Escherichia coli*.

BACKGROUND OF THE INVENTION

*Escherichia coli* is incapable of performing post-translational modifications; still, it has been the most common host system employed for the production of recombinant human therapeutic proteins. Among them, skin proteins including epidermal growth factor (EGF) and basic fibroblast growth factor (bFGF), which do not require post-translational modifications such as glycosylation for biological activities and stability, have been expressed in *E. coli* using various tactics.

Probably due to its small size, EGF has been efficiently expressed, secreted and even excreted to the culture medium in *E. coli*. Excreted EGF was not only demonstrated to be bioactive, but more importantly, it was also shown to possess the correct primary (authentic) structure. Furthermore, EGF produced by excretion is free from endotoxin contamination as production of it through excretion does not require cell disruption. In addition, the low level of cytoplasmic proteins in the medium greatly facilitates the purification of EGF to high homogeneity. Importantly, the process is highly reproducible and easily scalable.

With respect to bFGF, despite its secretory nature, it has not been successfully expressed through either secretion or excretion in *E. coli*. Conventionally, expression of bFGF in *E. coli* has been confined to the cytoplasm using a fusion approach, in which retrieval of bFGF relies on cell lysis, proteolytic digestion of the fusion intermediate, and subsequent purification commonly accomplished by affinity chromatography. Intracellular expression of bFGF incurs high production costs as it requires either an expensive protease to cleave the fusion product or a labor-intensive protocol to regenerate bFGF when inclusion aggregates formed. Despite these manipulations, bFGF expression in *E. coli* has not been satisfactorily fulfilled as the resulting product was shown to be incorrectly processed or biologically inactive.

There had been attempts to use other recombinant systems to produce bFGF. One such attempt concerns the engineering of *Bacillus subtilis* to facilitate secretory production of bFGF. With the use of the NPR signal peptide of a *B. amyloliquefaciens* protease gene, which enabled accurate peptidase processing of the fusion precursor, together with a facile cell-wall destabilization protocol, bFGF possessing the authentic structure and full bioactivity was shown to be secreted into the culture medium in *B. subtilis*.

The present invention provides an alternative and/or an improved methodology and system for producing bFGF and/or other useful polypeptides reliably and efficiently.

SUMMARY OF THE INVENTION

According to a first aspect of the present invention, there is provided a DNA construct for use in an *Escherichia coli* host for production of at least a first polypeptide, wherein the first polypeptide is an authentic basic fibroblast growth factor (bFGF), and wherein the DNA construct comprises an insert including, in the sequence of an expression cassette, an intein sequence and DNA coding for basic fibroblast growth factor (bFGF), wherein the DNA construct is configured to render the host to secrete the basic fibroblast growth factor (bFGF) in the cytoplasm of the host and/or excrete to cell medium in which the host is cultured.

Preferably, the DNA may comprise DNA coding for a second polypeptide, wherein the DNA coding for the second polypeptide may be arranged between the expression cassette and the intein sequence. The DNA coding for the second polypeptide may be coding for authentic human epidermal growth factor (EGF). The DNA construct may be configured to render the host to secrete the first and/or second polypeptides as non-fused polypeptide.

In an embodiment, the intein sequence may be Sce VMA intein sequence.

In one embodiment, the expression cassette may include, a promoter sequence, an operator sequence, a sequence for consensus ribosome binding site and a leader sequence. In a specific embodiment, the expression cassette may include, in the sequence of a promoter sequence, an operator sequence, a sequence for consensus ribosome binding site and a leader sequence. In another specific embodiment, the promoter sequence may be lacUV5 promoter (lacUV5), the operator sequence may be lac operator (lacO), and the leader sequence may be the ompA leader sequence (ompA).

According to a second aspect of the present invention, there is provided an engineering biological system for the production of at least basic fibroblast growth factor (bFGF), wherein the system is an *Escherichia coli* host, and wherein the system is adapted to produce basic fibroblast growth factor (bFGF) by secretion into the cytoplasm and/or into cell culture medium in which the system is cultured.

Preferably, the system may comprise a DNA construct as described above.

The system may be configured to produce the first polypeptide as a non-fused polypeptide.

The system may be configured to produce the second polypeptide as a non-fused polypeptide.

According to a third aspect of the present invention, there is provided a method of producing basic fibroblast (bFGF) as an extracellular product from and/or cytoplasm in an *Escherichia coli* host, comprising a step of employing an intein in a DNA construct for facilitating expression of the bFGF.

Preferably, the intein may be Sce VMA intein.

In an embodiment, the method may be adapted to co-express bFGF and authentic human epidermal growth factor (EGF) in the same *Escherichia coli* host as non-fused polypeptides.

In one embodiment, the method may comprise a step of producing bFGF and/or EGF in the cytoplasm of the host and/or cell medium in which the host is cultured.

The method may preferably provide a step of positioning the intein between DNA coding sequences of bFGF and EGF in the DNA construct.

In an embodiment, DNA codings of bFGF and EGF may be positioned in the same DNA construct.

BRIEF DESCRIPTION OF THE DRAWINGS

FIG. 1 is a schematic representation showing DNA constructs employed in the studies leading to the present invention. Upper portion of the figure shows three plasmids employed, namely (A) pWKW2FGFR, (B) pWKW20VMA, and (C) pWK3R. Symbols for genetic elements are as follows: bgf=bFGF gene; VMA=coding sequence of the Sce VMA intein; egf=EGF gene; ori=origin of replication in E. coli; amp$^R$=ampicillin resistance gene. Lower portion of the figure shows the 5'-terminal region of the LacUV5 expression cassette "  " comprising the lacUV5 promoter (lacUV5), the lac operator (lacO), the consensus ribosome binding site (RBS), and the ompA leader sequence (ompA). Arrow indicates the direction of transcription from the lacUV5 promoter. The arrow designates the direction of transcription from the lacUV5 promoter. The DNA coding sequence and amino acid sequences at the VMA intein-fusion boundaries in constructs pWKW20VMA and pWK3R were revealed in panel (D) located in lowest portion of the figure;

FIG. 2 is a photographic representation of Western blot analysis of bFGF and EGF expressed by various plasmids constructs. E. coli cultures harboring the three constructs: pWK3R, pWKW20VMA and pWKW2FGFR grown under IPTG induction for 8 h were fractionated into cell supernatant (SN) and cell lysate (CL) preparations. The samples were analyzed for bFGF and EGF products by Western blotting with antibodies raised against: [Gel A] bFGF and MazG (internal control); [Gel B] bFGF, EGF and MazG. The samples were also stained with Coomassie Brilliant Blue R-250 and revealed on [Gel C]. The premature bFGF (OmpA-bFGF) and premature EGF (OmpA-EGF) intermediates are indicated, whereas the mature bFGF (Mat-bFGF) and mature EGF (Mat-EGF) products are also denoted. The amounts of SN and CL samples loaded were equivalent to 10 μl and 5 μl of cell culture, respectively. The names of the three constructs are shown beneath the gels to indicate the cell cultures wherefrom the fractionated samples were prepared. The precursors: OmpA-EGF-VMA-bFGF (Δ) and EGF-VMA-bFGF (■) revealed in FIG. 2a (lanes 2 and 3) and FIG. 2b (lanes 3 and 4) are denoted. Other symbols used are: M=protein markers; +VE=bFGF or bFGF plus EGF standards employed as positive controls;

DESCRIPTION OF PREFERRED EMBODIMENTS OF THE PRESENT INVENTION

E. coli has been employed for extracellular production of a large collection of naturally secretory proteins of different origins, functions and sizes. Research leading to the present invention provides mechanism for expressing authentic bFGF by cellular secretion/excretion in E. coli which was not possible or at least not reliable before. As will be explained hereinafter, the present invention makes use of an innovative strategy, making use of a concerted effort between an efficient excretion construct, pWKW2, and the self-cleavable Sce VMA intein, to promote secretory expression of bFGF in E. coli. Data from the research demonstrates, for the first time, that authentic bFGF can be and is produced reliably and/or with improved efficiency as an excreted product in E. coli. Moreover, EGF can also be co-excreted to the culture supernatant (SN). Remarkably, and unexpectedly, both polypeptide factors are also identified in the cell lysate (CL), and they are revealed to be identical to their excreted counterparts. Even more unexpectedly, both EGF and bFGF retrieved from SN and CL are confirmed to be fully bioactive and authentic in terms of their primary structures. Importantly, the results of our present invention support the notion that the two subcellular compartmental fractions together present a remarkable resource for the cost-effective production of superb quality EGF and bFGF. For the excreted bFGF, or EGF, the polypeptide has already undergone in situ cellular cleavage and there is no need for subsequent processing by, for example, cleavage with help of an affinity column.

Experiments and Results

Engineering of DNA Constructs

Figure 1:
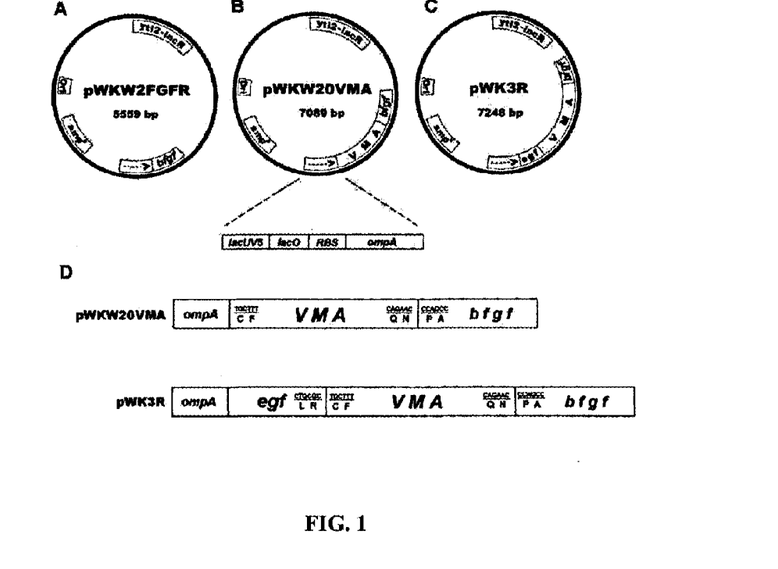

In the research leading to the present invention, pWKW2 was employed as the expression vector to result in three new DNA constructs for secretory/excretory expression of EGF and/or bFGF in E. coli. In the first construct, pWKW2FGFR (FIG. 1a), the bgf gene was cloned, by replacing the egf gene, and fused in-frame with the ompA leader sequence. To form the second construct, pWKW20VMA (FIG. 1b), the coding sequence of the Sce VMA intein (VMA), was inserted right between the ompA leader sequence and the bgf gene in pWKW2FGFR. To obtain the final construct, pWK3R (FIG. 1c), a DNA insert comprising the coding sequence of VMA and the bgf gene was fused in-frame with the egf gene in pWKW2.

Figure 2:
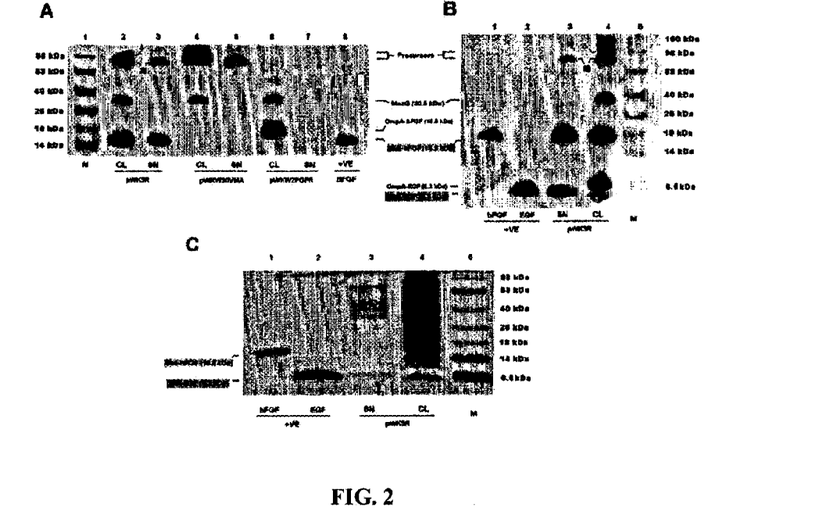

Expression of bFGF and EGF in E. coli Transformants Harboring the Three Plasmids Although pWKW2 was employed to provide efficient excretion of EGF, its first derivative harboring the bfgf gene, pWKW2FGFR (FIG. 1a), was unable to offer similar performance (FIG. 2a). The bFGF product resulting from pWKW2FGFR expression was shown to be essentially confined within the cell, i.e. suggesting that it is not excretory, existing as an OmpA secretion signal (OmpA)-bFGF fusion (FIG. 2a, lane 6). The observation suggested that the OmpA-bFGF fusion might not be well equipped for secretion.

Research has shown that signal peptides fused with inteins, e.g. VMA, would enable low levels of secretion of recombinant proteins. To ascertain the effectiveness of signal peptides fused with inteins such as VMA in secretory production of bFGF, in our research leading to the invention the coding sequence of VMA was inserted between the bfgf gene and the ompA leader in pWKW2FGFR to form pWKW20VMA (FIG. 1b). Western blot analysis of bFGF expression in a JM101 [pWKW20VMA] culture revealed that only a low level of bFGF, essentially in form of a large (~73 kDa) uncleaved VMA-bFGF intermediate (VMA-bFGF), was present in the culture medium (FIG. 2a, lane 5). Similarly, the precursor of VMA-bFGF, OmpA-VMA-bFGF, was also detected as a non-cleavable polypeptide in the cytoplasm (FIG. 2a, lane 4). Changes in environmental conditions did not show to have any beneficial impact on cleavage efficiencies between VMA and its flanking sequences (data not shown). Presumably, neither VMA-bFGF nor OmpA-VMA-bFGF was able to form a self-cleavable intermediate. Nonetheless, despite the large size and intracellular origin of VMA, excretion of VMA-bFGF was shown to be possible in E. coli in our research.

Our further research shows that an efficient secretory protein should possess two functionalities, namely, first, as an "engine" to facilitate secretion/excretion of VMA-bFGF, and second, as a compatible "N-terminal extein" of VMA-bFGF, thus enabling the latter to perform self-cleavage activities before excretion. In view of the superb performance of pWKW2 in EGF expression in our research, the present invention adopts the DNA sequence encoding VMA-bFGF fused in-frame with the egf gene, which was previously cloned next to the ompA leader in the LacUV5 expression cassette, to form construct pWK3R (FIG. 1c). Western blot analysis has revealed that not only bFGF can be efficiently excreted to the culture supernatant (SN) (FIG. 2a, lane 3), but also a high level of EGF was also detected in the same medium (FIG. 2b, lane 3). Moreover, both factors were revealed as processed non-fused products (FIG. 2). The failure to detect the cytoplasmic marker, MazG, in SN supports the conclusion, unexpectedly, that both detected EGF and bFGF there were attributed to excretion instead of cell lysis (FIG. 2A, lane 3 and FIG. 2B, lane 3).

Subcellular Location of bFGF and EGF in JM101 [pWK3R]

In order to appreciate the distribution of bFGF and EGF expressed in E. coli harboring pWK3R, further studies were performed. Specifically, an IPTG induced JM101 [pWK3R] culture was harvested after 8 h of induction and processed to obtain cell lysate (CL) and SN fractions. It was exciting to note that high levels of non-fused bFGF were detected in both SN (FIG. 2a, lane 3) and CL (FIG. 2a, lane 2), indicating that cleavage of bFGF from VMA occurred in both the intracellular and extracellular fractions of the E. coli culture.

On the other hand, in our studies EGF was also found to be efficiently expressed and excreted into SN of the JM101 [pWK3R] culture (FIG. 2b, lane 3). Nonetheless, despite the high level of excreted EGF, a significant level of processed EGF, in conjunction with the uncleaved OmpA-EGF intermediate, was also detected in CL (FIG. 2b, lane 4).

Authenticity of bFGF and EGF from JM101 [pWK3R]

The processed bFGF product purified from both CL and SN of the induced JM101 [pWK3R] culture (described above) was analyzed by liquid chromatography-tandem mass spectrometry for ascertaining its authenticity. As demonstrated by the results, the bFGF product from both fractions contained identical N- and C-terminal sequences as those of native bFGF (Table 2), indicating that its excision from the two precursors: OmpA-EGF-VMA-bFGF (in the cytoplasm) (FIG. 2a, lane 2) and EGF-VMA-bFGF (in the medium) (FIG. 2a, lane 3), was automatic and precise to result in authentic bFGF successfully.

Figure 3:
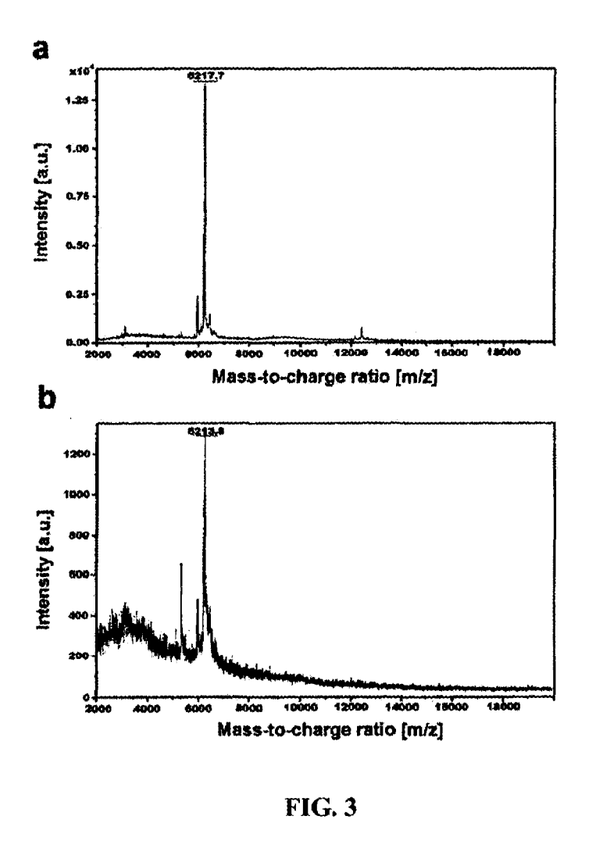
FIG. 3 is concerned with two graphs showing mass determination of purified EGF by MALDI-TOF. The profiles resulting from the analysis (see Methods) of: (a) commercial EGF standard possessing native primary structure; (b) EGF purified from SN of a JM101 [pWK3R] culture (see Methods for growth and induction conditions) are shown. A prominent peak, with a mass-to-charge ratio (m/z) at the 6213 to 6217 region, expected to be derived from authentic EGF in both plots is denoted. [a.u.] represents arbitrary unit.

Although the OmpA-EGF fusion was shown to be processed precisely to yield authentic EGF in the culture medium of JM101 [pWKW2], it is interesting to discern whether EGF retrieved from the cleavage of the EGF-VMA-bFGF intermediate in SN (FIG. 2b, lane 3) was structurally different from native EGF. As supported by mass determination, it was concluded that the retrieved EGF and native EGF are identical (FIG. 3).

Potency of bFGF and EGF from JM101 [pWK3R]

Samples of bFGF and EGF purified from SN of JM101 [pWK3R] were further scrutinized and assayed for bioactivities, with reference to their authentic counterparts previously expressed and characterized by our research group. The results revealed that both products shared apparently the same potency as the standards (FIG. 4), supporting the conclusion that excreted bFGF and EGF in JM101 [pWK3R] are not only authentic but also fully bioactive. Since the bFGF component purified from CL was revealed to be structurally identical to its SN counterpart (Table 2), it means that the former was equally potent as the latter.

Expression of bFGF and EGF in JM101 [pWK3R]

Figure 4:
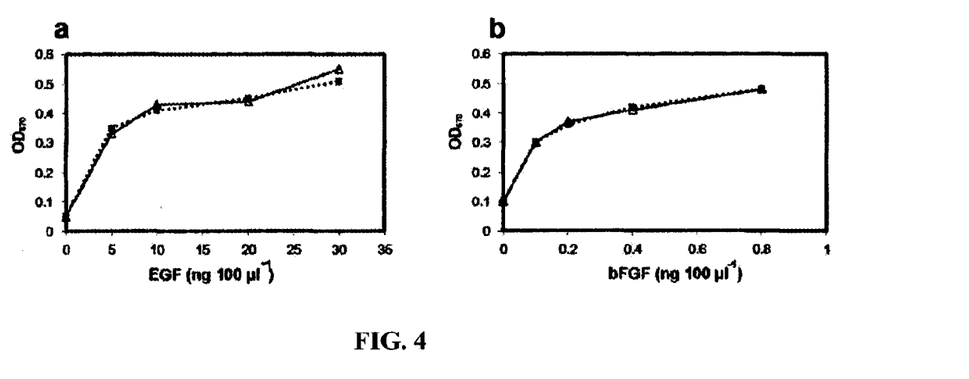
FIG. 4 is concerned with two graphs showing bioassays of EGF and bFGF. Mature EGF and bFGF samples were purified from the culture supernatant of an induced JM101 [pWK3R] (see Methods for growth and induction conditions). The assays for mitogenic effects of EGF and bFGF on the proliferation of BALB/C 3T3 fibroblast cells were described in Methods. The bioactivities of the two mature factors ( ⋯▩⋯ ) were compared with that of EGF and bFGF standards ( ⋯Δ⋯ ) possessing correct primary structures. Both assays yielded superimposable curves. Each assay was repeated four times (σ<0.05)

Cell samples of JM101 [pWK3R] grown under IPTG induction for 8 h were harvested and prepared for CL and SN fractions. Western blot analysis of bFGF and EGF in the two fractions revealed that both factors or polypeptides were efficiently expressed in the culture. More importantly, the intermediate products: OmpA-EGF-VMA-bFGF identified in CL (FIG. 2a, lane 2) and EGF-VMA-bFGF in SN (FIG. 2a, lane 3), were both processed precisely to yield authentic bFGF. Combining both fractions, an impressive yield, ca. 103 mg $l^{-1}$, of bFGF was attained (FIG. 4). Similarly, high levels of authentic EGF, ca. 38 mg $l^{-1}$ in SN (FIG. 2b, lane 3; FIG. 4) and ca. 36 mg $l^{-1}$ in CL (FIG. 2b, lane 4), were also obtained.

Another noteworthy observation is that JM101 [pWK3R] retained good growth rates throughout the time-course study, despite efficient expression and secretion of a mixture of intermediates (FIG. 5): OmpA-EGF-VMA-bFGF, OmpA-EGF-VMA and OmpA-EGF, taking place in the culture (FIG. 2a, lanes 2 and 3; FIG. 2b. lanes 3 and 4). It remains to be clarified why secretory expression of a protein complex as specified above is only as debilitating as that of a homogeneous population comprising purely of the much smaller OmpA-EGF intermediate reported earlier.

Discussion

In the past, expression of bFGF in E. coli was generally limited to the use of a conventional fusion method, in which the intracellular fusion intermediate was subsequently retrieved and cleaved with a protease to release bFGF at best as a derivative. The additional and manual step of cleavage was cumbersome, costly and would introduce uncertainties.

The present invention has employed E. coli to efficiently express bFGF as a secretory protein, and more importantly, the recombinant bFGF and its native counterpart shared the same protein sequence. The results as described above supports our findings that extracellular expression, in which E. coli can also serve as a potential host. The present invention has thus provided a technically feasible and cost-effective alternative for the production of authentic bFGF.

We have previously developed an efficient excretion E. coli system, JM101 [pWKW2], to facilitate production of authentic EGF. The present invention as depicted above has demonstrated the application of construct pWKW2 to the engineering of a versatile E. coli system for successful expression of bFGF as a non-fused product having an authentic structure (Table 2) and potent bioactivity (FIG. 4). Moreover, it is shown that authentic and bioactive EGF (FIG. 3 and FIG. 4) can also be co-expressed in the same host efficiently.

Direct fusion of the bfgf gene (by replacing the efg gene) to the ompA leader in pWKW2 would not lead to efficient excretory production of bFGF (FIG. 2a, lanes 6 and 7) as observed previously in EGF expression. Interestingly, and unexpectedly, an insertion of VMA between OmpA and bFGF, results in excretory production of the large (~73 kDa) VMA-bFGF intermediate in SN (FIG. 2a, lane 5). It was quite unexpected that VMA, being an intracellular protein, did not hamper secretion of OmpA-VMA-bFGF in JM101 [pWKW20VMA] (FIG. 1). Nevertheless, further processing of VMA-bFGF in SN was prohibited (FIG. 2a, lane 5); presumably because the large size of VMA physically interfered with the cleavage process.

However, intriguingly, by adding EGF to the N-terminus of VMA-bFGF, both secretion and cleavage of the latter is shown to be enhanced (FIG. 2a, lane 3; FIG. 2b, lane 3). Despite being larger in size, it is shown that the resulting intermediate, EGF-VMA-bFGF, is secreted and cleaved much more efficiently than VMA-bFGF was to yield not only bFGF, but also EGF, as excreted products (FIG. 2b, lane 3). It appears that the OmpA-EGF-VMA-bFGF precursor can attain an extended structure, which is shown to be more efficiently secreted to yield EGF-VMA-bFGF (FIG. 2a, lane 2; FIG. 2b, lane 4).

The presence of a proline residue at the cleavage point of an intein might interfere with cleavage at that point. Interestingly, despite the proline residue found at the N-extein of bFGF (FIG. 1D), the cleavage between VMA and bFGF in precursors OmpA-EGF-VMA-bFGF and EGF-VMA-bFGF took place quite efficiently in a JM101 [pWK3R] culture, giving rise to EGF and bFGF in both SN and CL fractions (FIGS. 2A and 2B). Presumably, despite the presence of proline, which tends to introduce a "kink" into a helical structure of proteins, the precursor would present an extended, thus a more open, structure to facilitate the cleavage process. Furthermore, since the intermediate, VMA-bFGF, which appeared to be non-cleavable (FIG. 2A, lane 6), the absence of it as an intermediate in neither CL nor SN of JM101 [pWK3R] (FIG. 2A, lanes 2 and 3) supported the hypothesis that the cleavage of bFGF from precursors OmpA-EGF-VMA-bFGF and EGF-VMA-bFGF took place either earlier than or simultaneously with that of EGF.

It is also noteworthy that the cleavage of precursors OmpA-EGF-VMA-bFGF and EGF-VMA-bFGF took place spontaneously in both SN and CL fractions (FIGS. 2A and 2B). The demonstration of in situ cleavage of EGF and bFGF from precursors OmpA-EGF-VMA-bFGF and EGF-VMA-bFGF and the recovery of high levels of both polypeptides from SN and CL preparations presents a facile method to retrieve target proteins derived from intein-mediated expression. However, our results are apparently contradictory to previous findings in which the release of the exteins from VMA fusions was shown to require the use of a reducing agent and/or low pH. Despite the potential usefulness of our observation, it remains to be elucidated whether the cleavage activities detected in SN and CL are attributable to the extended structures of the two precursors postulated above or there are other explanations for their manifestation.

Nonetheless, the fusion proteins engineered in this study may be employed as excellent model proteins for the study of effects of changes in flanking sequences on cleavage of VMA. Thus far, the influence of extein contexts on cleavage of inteins is poorly understood.

Soon after OmpA-EGF-VMA-bFGF was expressed in JM101 [pWK3R], this large (~82 kDa) precursor would either remain in the cytoplasm or enter the secretion pathway; concurrently, it would be processed at the two cleavage sites flanking VMA to give rise to smaller intermediates including OmpA-EGF-VMA, OmpA-EGF, VMA-bFGF and bFGF; the first two intermediates were expected to be secretory, and the last two would stay in the cytoplasm. Notably, the bFGF molecule, which was shown to be correctly processed to yield an authentic structure (Table 2), was identified to be co-existed in both SN and CL (FIG. 2a, lanes 2 and 3). This novel finding may provide new insight into expression of mature secretory proteins in the cytoplasm without the requirement of going through the expensive and labor-intensive conventional fusion procedures.

Figure 5:
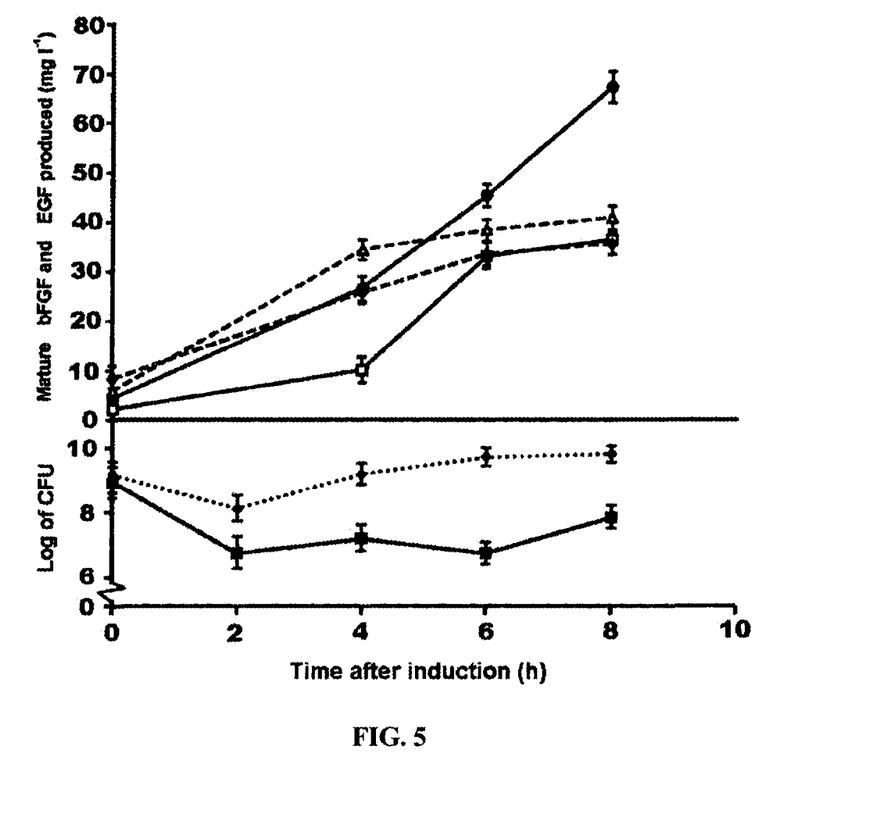
FIG. 5 is concerned with two graphs showing co-expression of mature bFGF and mature EGF in a JM101 [pWK3R] culture. The conditions for growth and induction of the JM101 [pWK3R] culture are described in Methods. Top panel: concentrations of mature bFGF in SN (—□—), mature bFGF in CL ( —●— ), mature EGF in SN (- -Δ- -), and mature EGF in CL (==◆==) are shown. The results shown are mean±SEM values from 4 different experiments. Bottom panel: viable cell counts obtained on plain agar plates ( ⋯◆⋯ ) and agar plates supplemented with Amp ( —■— ) are shown; CFU refers to cell forming units.

Altogether, the OmpA-EGF-VMA-bFGF precursor and its intermediates formed two separate pools of mature bFGF and EGF, one being the secreted pool and the other being the intracellular one. It is noteworthy that the cell pellet of JM101 [pWK3R] represented an even larger reserve of bFGF than its secreted counterpart (FIG. 2a, lanes 2 and 3; FIG. 5). Moreover, a significant level of processed EGF was also detected in CL. Presumably, the processed EGF detected in CL was trapped subsequent to peptidase cleavage in the SecYEG pathway. Similar to the findings of our previous research on protein excretion, only low levels of EGF and bFGF were detected in the periplasm (data not shown). These results support the view that cleavages of OmpA-EGF-VMA-bFGF took place efficiently in the cytoplasm to release bFGF. Previous attempts employing inteins to form EGF fusions, however, resulted in the formation of insoluble aggregates in the cytoplasm of E. coli. Despite the high level of OmpA-EGF-VMA-bFGF, which was expressed under the control of the fine-tuned LacUV5 cassette in pWKW2, the ability of this large precursor to stay soluble in the cell was crucial for the subsequent attainment of both EGF and bFGF as bioactive and authentic products.

On the other hand, despite the large size of OmpA-EGF-VMA-bFGF (FIG. 2B, lane 4), it can be readily secreted, presumably, through the SecYEG translocation machinery, to form an excreted intermediate: EGF-VMA-bFGF (FIG. 2B, lane 3). However, it is shown that the excreted intermediate can be bestowed with efficient self-cleavage activities to result further in authentic bFGF and EGF (FIG. 2B, lane 3). In general, cytoplasmic proteins, which have been speculated to form folded structures, are not qualified to enter the secretion pathway. Therefore, it appears that with EGF and bFGF serving as N-terminal and C-terminal exteins in EGF-VMA-bFGF flanking VMA, the tendency of VMA to fold was overridden and prevented. The consequence is that EGF-VMA-bFGF can acquire an extended structure which is competent for secretion. These findings are important for expression of a wide range of intracellular proteins, which might otherwise be ended up as fusion proteins or inclusion bodies if cytoplasmic expression was the only choice.

In conclusion, the versatile E. coli system introduced in this disclosure has been shown to be an efficient manufacturing plant co-expressing at least authentic EGF and bFGF, or other proteins.

Methods

Bacterial Strain & Chemicals

E. coli strain JM101 was the host employed in this study. The Phusion PCR Kit, restriction, and modifying enzymes were purchased from New England Biolabs (Ipswich, Mass., USA). All oligos were purchased from Invitrogen (Carlsbad, Calif., USA). Other chemicals were purchased from Sigma-Aldrich Corporation (St. Louis, Mo., USA) unless otherwise specified. Antibodies against bFGF and EGF and MazG serving as a cytoplasmic marker were raised in rabbits.

Construction of Expression Constructs

Plasmids pWKW2FGFR, pWKW20VMA, and pWK3R were constructed as derivatives of pWKW2, with the following modifications. An EcoRI-EcoRI fragment containing the LacUV5 expression cassette in which the egf gene was harbored, was removed. The same cassette containing the bfgf gene was first synthesized by overlap extension PCR using oligos P1-P5 (Table 1) as primers and vectors pSO and pWKW2 as templates, followed by EcoRI restriction and relegation with pWKW2 to generate plasmid pWKW2FGFR (FIG. 1a). Plasmid pWKW20VMA (FIG. 1b), in which the Sce VMA intein of a Saccharomyces cerevisiae vascular membrane ATPase gene was fused upstream with bfgf, was constructed by first performing overlap extension PCR using constructs pTYB21 and pWKW2FGFR as templates and oligos P6-P9 (Table 1) as primers to form the expected cassette, followed by restricting the cassette with NruI and BamHI and ligating it with pWKW2FGFR. To obtain plasmid pWK3R (FIG. 1c), the expression cassette was first engineered employing overlap extension PCR with pWKW2 as template and oligos P10-P11 (Table 1) as primers, followed by restriction with NruI and KpnI and ligation with pWKW20VMA.

Shake Flask Cultivations

E. coli transformants were grown at 34° C. in MMBL medium supplemented with 70 µg ml$^{-1}$ of ampicillin. In time-course experiments, a 250 ml flask containing 50 ml of growth medium was inoculated with a freshly grown colony and shaken at 250 rpm and 34° C. until the culture reached a density of $A_{550}$=8. Subsequently, 0.1 mM IPTG was added and the culture was continuously grown for 8 h. Afterwards, the culture was centrifuged and the supernatant (SN) was saved. The cell pellet was resuspended in 120 µl of Tris.Cl buffer (50 mM, pH 8.0), followed by an addition of 83 µl of EDTA solution (0.25 M, pH 8.0). The cell mixture was incubated on ice for 5 min and then treated with 120 µl of lysozyme solution (10 mg ml$^{-1}$) at 37° C. for 20 min. After addition of 83 µl of lysis buffer (10 mM EDTA, 10% Triton X-100, and 50 mM Tris.Cl, pH 8.0), the tube was inverted gently, followed by spinning at 13,000 rpm for 10 min. The supernatant was the cell lysate (CL). Both SN and CL fractions were analyzed for bFGF and EGF by Western blot analysis, of which the images were quantified by densitometry using the ImageJ software (National Institutes of Health, USA).

Ammonium Sulfate Precipitation

Ammonium sulfate was added to SN containing bFGF to reach 35% saturation. After centrifugation, the precipitate (labelled A), which contained bFGF activities, was dissolved in 5 ml of 50 mM Tris.Cl (pH 7.5) for subsequent purification. As for the supernatant, ammonium sulfate was added to it to attain 65% saturation. The precipitate (labelled B), which contained EGF activities, was collected by centrifugation and dissolved in 5 ml of phosphate buffer (PB; 1.44 g $Na_2HPO_4$ and 0.24 g $KH_2PO_4$ per liter, pH 7.4) for later use.

Cell Lysis

The cell pellet obtained from a 400 ml culture (see Shake flask cultivations above) was dissolved in 50 mM Tris.Cl (pH 7.5), and the resuspension was processed 5 times with a cell disruptor system (Constant Systems Ltd.) using a pressure set at 25 kPa. The lysate was centrifuged at 13,500 rpm for 10 min and the supernatant was saved for the purification of intracellular bFGF.

Purification of EGF

The purification of EGF using QAE Sephadex A-25 (Amersham Pharmacia) ion-exchange chromatography was described previously. The fractions containing EGF activities were pooled and filtered with an Amicon centrifugal filter unit (10 kDa cut-off) (Millipore). Afterwards, the filtrate was clarified through a Vivaspin 500 centrifugal filter unit (3 kDa cut-off) (GE healthcare) by centrifugation at 13,500 rpm for 1 h.

Analysis of EGF

The purified EGF was analyzed using a Bruker ultrafleXtreme MALDI-TOF/TOF mass spectrometer (Bruker Daltonics, Bremen, Germany) equipped with a smartbeam-II laser operated at 355 nm. The FlexControl (version 3.3, Bruker Daltonics) software was used to control the operation of the instrument. The MALDI laser intensity was tuned by the operator to obtain the optimal intensity and the resolution of mass spectra. One µl of sample was premixed with 1 µl of the matrix, Sinapinic acid (Bruker Daltonics), and the mixture was then spotted onto the Ground Steel Target plate (Bruker Daltonics). External calibration was performed using the Protein Calibration Standard I (Bruker Daltonics). Positive ion mass spectra were acquired in a linear mode for the mass spectrometry experiments.

Purification and Analysis of bFGF

The purification of bFGF using heparin-agarose chromatography and analysis of the purified bFGF by liquid chromatography tandem mass spectrometry were described previously.

Biological Assays of EGF and bFGF

The mitogenic effects of purified EGF and rbFGF on the proliferation of BALB/C 3T3 fibroblast cells were analyzed by the MTT assay as described previously. In short, BALB/C 3T3 cells were seeded in 96-well plates at a density of $5 \times 10^4$ cells and cultured in DMEM medium supplemented with 1.5% Fetal Bovine Serum at 37° C. for 24 h. Afterwards, the cells were incubated for 3 days separately with the following mixtures: (1) DMEM+EGF sample; (2) DMEM+commercial EGF; (3) DMEM+bFGF sample; (4) DMEM+commercial bFGF[21]; (5) DMEM. Subsequently, 20 µl of MTT solution (3-(4,5-Dimethylthiazol-2-yl)-2,5-diphenyltetrazolium bromide) was added to each well, followed by incubation of the plates at 37° C. for 4 h. The liquid was removed from each well, which was then added with 150 µl DMSO to dissolve the purple crystal. The plates were read at 570 nm using a microplate reader. The same assay was repeated four times. The reduction of MIT by NADPH-reductases activities produced by growing cells, which results in the formation of purple formazan (measured at OD 570 nm), provides a means to help quantify cell proliferation.

It should be understood that certain features of the invention, which are, for clarity, described in the content of separate embodiments or experiments, may be provided in combination in a single embodiment or experiment. Conversely, various features of the invention which are, for brevity, described in the content of a single embodiment or experiment, may be provided separately or in any appropriate sub-combinations. It is to be noted that certain features of the embodiments or experiments are illustrated by way of non-limiting examples. Also, a skilled person in the art will be aware of the prior art which is not explained in the above for brevity purpose.

The following references are incorporated by reference in their entirety.

Aliboandi M, Mirzahoseini H (20111 Purification and refolding of overexpressed human basic fibroblast growth factor in *Escherichia coli*. Biotechnol Res Int 2011:1-6

Andrades J A, Santamaria J A, Wu L T, Hall F L, Nimni M E, Becerra J (2001) Production of a recombinant human basic fibroblast growth factor with a collagen binding domain. Protoplasma 218:95-03

Asubel F, Brent R, Kingston R, Moore D, Seidman J, Smith J, Strobl K (1993) Curr Protoc Mol Biol 2:11.2.1-11.2.5

Barr P J, Cousens L S, Lee-Ng C T, Medina-Selby A, Masiarz F R, Hallewell R A, Chamberlain S H, Bradley J D, Lee D, Steimer K S (1988) Expression and processing of biologically active fibroblast growth factors in the yeast *Saccharomyces cerevisiae*. J Biol Chem 263:16471-16478

Bikfalvi A, Klein S, Pintucci G, Rifkin D B (1997) Biological Roles of Fibroblast Growth Factor-2. Endocr Rev 18:26-45

Chan A K N, Wang Y Y, Ng K L, Fu Z, Wong W K R (2012) Cloning and characterization of a novel cellobiase gene, cba3, encoding the first known 3-glucosidase of glycoside hydrolase family 1 of Cellulomonas biazotea. Gene 493: 52-61

Cottingham I R, Millar A, Emslie E, Colman A, Schnieke A E, McKee C (2001) A method for the amidation of recombinant peptides expressed as intein fusion proteins in *Escherichia coli*. Nat Biotechnol 19:974-977

Elleuche S, Pöggeler S (2010) Inteins, valuable genetic elements in molecular biology and biotechnology. Appl Microbiol Biotechnol 87:479-489

Esipov R S, Stepanenko V N, Chupova L A, Boyarskikh U A, Filipenko M L, Miroshnikov A I (2008) Production of recombinant human epidermal growth factor using Ssp dnaB mini-intein system. Protein Expr Purif 61:1-6

Ferrer-Miralies N, Domingo-Espín J, Corchero J L, Vázquez E, Villaverde A (2009) Microbial factories for recombinant pharmaceuticals. Microb Cell Fact 8:17

Fu Z B, Ng K L, Lam T L, Wong W K R (2005) Cell death caused by hyper-expression of a secretory exoglucanase in *Escherichia coli*. Protein Expr Purif 42:67-77

Fu Z B, Ng K L, Lam C C, Leung K C, Yip W H Wong W K R (2006) A two-stage refinement approach for the enhancement of excretory production of an exoglucanase from *Escherichia coli*. Protein Expr Purif 48:205-214

Garke G, Deckwer W D, Anspach F B (2000) Preparative two-step purification of recombinant human basic fibroblast growth factor from high-cell-density cultivation of *Escherichia coli*. J Chromatogr B Biomed Sci Appl 737: 25-38

Huang R C, Lam E, Chen Y H, Hackett J, Lam T L, Liu D, Ma M C, Siu K L, Sivakesava S, Xu Z N, Wong R S C, Wong W K R (1999) Human epidermal growth factor excreted by recombinant *Escherichia coli* K-12 has the correct N-terminus and is fully bioactive. Process Biochem 35:1-5

Ingham A B, Sproat K W, Tizard M L V, Moore R J (2005) A versatile system for the expression of nonmodified bacteriocins in *Escherichia coli*. J Appl Microbiol 98:676-683

Kwong K W Y, Ng K L, Lam C C, Wang Y Y, Wong W K R (2013) Authentic human basic fibroblast growth factor produced by secretion in *Bacillus subtilis*. Appl Microbiol Biotechnol 97:6803-6811

Lam T L, Wong R S C, Wong W K R (1997) Enhancement of extracellular production of a Cellulomonas fimi exoglucanase in *Escherichia coli* by the reduction of promoter strength. Enzyme Microb Technol 20:482-488

Lee C, Li P, Inouye H, Brickman E R, Beckwith J (1989) Genetic studies on the inability of beta-galactosidase to be translocated across the *Escherichia coli* cytoplasmic membrane. J Bacteriol 171:4609-4616

Li Y (2011) Self-cleaving fusion tags for recombinant protein production. Biotechnol Lett 33:869-881

Mirzahoseini H, Mehraein F, Omidinia E, Razavi M R (2004) Differential expression of human basic fibroblast growth factor in *Escherichia coli*: potential role of promoter. World J Microbiol Biotechnol 20:161-165

Mu X, Kong N, Chen W, Zhang T, Shen M, Yan W (2008) High-level expression, purification, and characterization of recombinant human basic fibroblast growth factor in *Pichia pastoris*. Protein Expr Purif 59:282-288

Nakayama A, Ando K, Kawamura K, Mita I, Fukazawa K, HoriM, Honjo M, Furutani Y (1988) Efficient secretion of the authentic mature human growth hormone by *Bacillus subtilis*. J Biotechnol 8:123-134

Sellke F W, Laham R J, Edelman E R, Pearlman J D, Simons M (1998) Therapeutic Angiogenesis With Basic Fibroblast Growth Factor: Technique and Early Results. Ann Thorac Surg 65:1540-1544

Sheng Z, Chang S B, Chirico W J (2003) Expression and purification of a biologically active basic fibroblast growth factor fusion protein. Protein Expr Purif 27:267-271

Sivakesava S, Xu Z N, Chen Y H, Hackett J, Huang R, Lam E, Lam T L, Siu K L, Wong R S C, Wong W K R (1999) Production of excreted human epidermal growth factor (hEGF) by an efficient recombinant *Escherichia coli* system. Process Biochem 34:893-900

Wang L, Kang J H, Kim K H, Lee E K (2010) Expression of intein-tagged fusion protein and its applications in downstream processing. J Chem Technol Biotechnol 85:11-18

Wang Y Y, Eu Z N, Ng K L, Lam C C, Chan A K N, Sze K F, Wong W K R (2011) Enhancement of excretory production of an exoglucanase from *Escherichia coli* with phage shock protein A (PspA) overexpression. J Microbiol Biotechnol 21:637-645

Wong W K R (2008) Application of recombinant microbial systems to the production of commercially valuable proteins. Res J Biotechnol 3

Wong W K R, Sutherland M L (1997) Excretion of heterologous proteins incR system of *Salmonella typhimurium*. J IndMicrobiol Biotechnol 21:31-36

Wong W K R, Lam E, Huang R C, Wong R S, Morris C, Hackett J (2001) Applications, and efficient large-scale production, of recombinant human epidermal growth factor. Biotechnol Genet Eng Rev 18: 51-71

Wong W K R, Ali A B, Ma M C (2003) Cloning, expression, and characterization of diuretic hormone Manduca diuresin from Manduca sexta in *Escherichia coli*. Protein Expr Purif 29: 51-57

Wong W K R, Lam K H, Tsang M W (2009) Method and composition for treating skinwounds with epidermal growth factor.

U.S. Pat. No. 7,517,528 Wong W K R, Fu Z B, Wang Y Y, Ng K L, Chan A K N (2012) Engineering of efficient *Escherichia coli* excretion systems for the production of heterologous proteins for commercial applications. Recent Patents Chem Eng 5:45-55

The invention claimed is:

1. A DNA construct for use in a *Escherichia coli* host for production of at least an authentic basic fibroblast growth factor (bFGF), wherein said DNA construct comprises an insert including an expression cassette, an intein sequence, a DNA coding for basic fibroblast growth factor (bFGF), and a DNA coding for authentic human epidermal growth factor (EGF), wherein said DNA construct is configured to render the host to secrete the basic fibroblast growth factor (bFGF) in the cytoplasm of the host and/or to excrete to cell medium in which the host is cultured.

2. A DNA construct as claimed in claim 1, wherein said DNA coding for EGF is arranged between said expression cassette and said intein sequence.

3. A DNA construct as claimed in claim 2, configured to render the host to secrete or excrete the bFGF and/or the EGF as non-fused polypeptide.

4. A DNA construct as claimed in claim 1, wherein said intein sequence is Sce VMA intein sequence.

5. A DNA construct as claimed in claim 1, wherein said expression cassette includes, a promoter sequence, an operator sequence, a sequence for consensus ribosome binding site and a leader sequence.

6. A DNA construct as claimed in claim 5, wherein said expression cassette includes, in the sequence of a promoter sequence, an operator sequence, a sequence for consensus rib some binding site and a leader sequence.

7. A DNA construct as claimed in claim 5, wherein said promoter sequence is lacUV5 promoter (lacUV5), said operator sequence is lac operator (lac0), and said leader sequence is the ompA leader sequence (ompA).

8. An engineering biological system for the production of at least basic fibroblast growth factor (bFGF) and human epidermal growth factor (EGF), wherein said system is an *Escherichia coli* host, and wherein said system is adapted to produce the basic fibroblast growth factor (bFGF) and the human epidermal growth factor (EGF) by secretion into the cytoplasm and/or excretion into cell culture medium in which said system is cultured.

9. A system as claimed in claim 8, comprising a DNA construct having an insert including an expression cassette, an intein sequence, DNA coding for basic fibroblast growth factor (bFGF) and DNA coding for human epidermal growth factor (EGF).

10. A system as claimed in claim 8, configured to produce the basic fibroblast growth factor (bFGF) as a non-fused polypeptide.

11. A system as claimed in claim 8, configured to produce the human epidermal growth factor (EGF) as a non-fused polypeptide.

12. A method of producing basic fibroblast (bFGF) and human epidermal growth factor (EGF) as extracellular products from and/or in the cytoplasm of an *Escherichia coli* host, comprising a step of employing an intein and DNA codings for the bFGF and EGF, respectively, in a DNA construct for expression of the bFGF and EGF.

13. A method as claimed in claim 12, wherein the intein is Sce VMA intein.

14. A method as claimed in claim 12, comprising a step of positioning the intein between the DNA codings of bFGF and EGF in the DNA construct.

15. A method as claimed in claim 12, wherein the bFGF and/or EGF produced are non-fused polypeptides.

* * * * *

SEQUENCE LISTING

<160> NUMBER OF SEQ ID NOS: 14

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caagaattcg catacttact ccccatcccc ctgtttacac                              40

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccgccatcc tctggcaagg ctggggcctg cgctacggta gcgaaacc                    48

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtttcgcta ccgtagcgca ggccccagcc ttgccagagg atggcggcag cggc             54

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaattctt aaaaaaaagc ccgctcatta ggcgggctgc ttaattaatt a                51

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 cttttcttc caatgtctgc taagagctaa tgaaattaat tcctgcaggc ttaattaatt        60
aagcagcccg cc                                                           72

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
ctatcgcgat tgcagtggca ctggctggtt tcgctaccgt agcgcaggcc tgctttgcca      60
agggtaccaa tgttttaatg                                                  80

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccgctgccg ccatcctctg gcaaggctgg gttctgtaca caacctgag atccaagcaa       60 aaac                                                                   64

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtttttgctt ggatctcagg ttgttgtaca gaacccagcc ttgccagagg atggcggcag      60
cggc                                                                   64

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctgttttgg atccaagttt atactgccca gtgcgtttc                             39

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagctatcgc gattgcagtg gcactggctg gtttcg                                36

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cattggtacc cttggcaaag cagcgcagtt cccaccactt caggtctcgg tac             53
```

```
<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Ala Leu Pro Glu Asp Gly Gly Ser Gly Ala Phe Pro Pro Gly His
1               5                   10                  15

Phe Lys

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ile Leu Phe Leu Pro Met Ser Ala Lys Ser
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gly Pro Gly Gln Lys Ala Ile Leu Phe Leu Pro Met Ser Ala Lys
1               5                   10                  15

Ser
```